United States Patent [19]

Alexander et al.

[11] Patent Number: 4,650,669

[45] Date of Patent: Mar. 17, 1987

[54] METHOD TO MAKE EFFERVESCENT CALCIUM TABLETS AND CALCIUM TABLETS PRODUCED THEREBY

[75] Inventors: Thomas A. Alexander, South Bend; Donald L. Peterson, Elkhart, both of Ind.

[73] Assignee: Miles Laboratories, Inc., Elkhart, Ind.

[21] Appl. No.: 760,685

[22] Filed: Jul. 30, 1985

[51] Int. Cl.$^4$ .......................... A61K 9/46; A61K 9/62; A61K 33/10

[52] U.S. Cl. ...................... 424/44; 424/466; 424/156

[58] Field of Search ............................ 424/44, 156, 35

[56] References Cited

U.S. PATENT DOCUMENTS

| | | | |
|---|---|---|---|
| 543,601 | 7/1895 | Kerfoot | 424/44 |
| 2,540,253 | 2/1951 | Garenheimer | 424/44 |
| 3,082,091 | 3/1963 | Smith et al. | 424/44 |
| 3,241,977 | 3/1966 | Mitchell et al. | 424/44 |
| 3,384,546 | 5/1968 | Palermo | 424/156 |
| 3,495,001 | 2/1970 | Leonards | 424/44 |
| 3,639,168 | 2/1972 | Monti et al. | 424/156 |
| 3,639,169 | 2/1972 | Broeg et al. | 424/156 |
| 3,882,228 | 6/1975 | Boncey et al. | 424/35 |
| 3,887,700 | 6/1975 | Boncey et al. | 424/44 |
| 3,962,417 | 6/1976 | Howell | 424/52 |
| 4,009,292 | 2/1977 | Finucane | 426/548 |
| 4,083,950 | 4/1978 | Duvall et al. | 424/44 |
| 4,083,951 | 4/1978 | Goudie et al. | 424/44 |
| 4,127,645 | 11/1978 | Witzel et al. | 424/44 |
| 4,237,147 | 12/1980 | Merten et al. | 426/590 |
| 4,327,076 | 4/1982 | Puglia et al. | 424/156 |
| 4,327,077 | 4/1982 | Puglia et al. | 424/156 |
| 4,349,542 | 9/1982 | Staniforth | 424/153 |
| 4,384,005 | 5/1983 | McSweeney | 426/250 |
| 4,446,135 | 5/1984 | Fountaine | 424/156 |
| 4,533,543 | 8/1985 | Morris et al. | 424/156 |

FOREIGN PATENT DOCUMENTS

| | | | |
|---|---|---|---|
| 3315800 | 10/1984 | Fed. Rep. of Germany | 424/156 |
| 59-199627 | 11/1984 | Japan | 424/156 |
| 39201913 | of 1913 | United Kingdom | 424/156 |
| 1292820 | 10/1972 | United Kingdom | 424/44 |

OTHER PUBLICATIONS

Robert R. Recker, M.D., "Calcium Absorption and Achlorhydria", The New England Journal of Medicine; Jul. 11, 1985, vol. 313, No. 2, pp. 70–73.

"The Absorption of Calcium Carbonate", Annals of Internal Medicine, vol. 66, No. 5, pp. 917–923, (Ivanovich, Fellow & Rich).

"Relation Between Gastric Secretion of Acid and Urinary Execretion of Calcium", Digestive Diseases and Sciences, vol. 28, No. 5, pp. 417–421.

*Primary Examiner*—Shep K. Rose
*Attorney, Agent, or Firm*—Jennifer L. Skord; Jerome L. Jeffers

[57] ABSTRACT

Described is a directly compressible formulation comprising calcium carbonate, citric acid, and a compression vehicle. In the preferred embodiment, the compression vehicle comprises a maltodextrin and lactose. The formulation can be compressed into an effervescent tablet system, which when placed in water effervesces in a relatively rapid dissolution releasing $CO_2$ and resulting in a solution of monocalcium citrate.

10 Claims, No Drawings

METHOD TO MAKE EFFERVESCENT CALCIUM TABLETS AND CALCIUM TABLETS PRODUCED THEREBY

The present invention relates to a method to make a granulation comprising calcium carbonate and a compression vehicle together with citric acid which allows the granulation composition to be easily compacted into a substantially stable, tablet dosage form intended as a nutrition aid or medicament. Thus, more particularly, the present invention involves coating certain vehicles onto particulate calcium carbonate so that when it is compressed with an organic acid such as citric acid to form a tablet, not only is the calcium carbonate/citric acid tablet storage stable, but also there is essentially no concomitant interference by the vehicle with the effervescent action of the citric acid and the calcium carbonate when the tablet is placed in water.

BACKGROUND OF THE INVENTION

It has long been known that calcium is a required nutriment for the human body. Not only does calcium enhance strong bones and teeth, but also in its carbonate salt form, it is useful in treating peptic ulcer disease. Moreover, several studies in the last few years have confirmed that post-menopausal women have a tendency toward osteoporosis, and thus need to take calcium.

Accordingly, calcium carbonate, one of the more readily available calcium salts has been widely used as a dietary supplement. Calcium carbonate is more acid soluble than other calcium salts, such as the saccharide salts. Furthermore, saccharides, for instance calcium gluconate, obviously have a lower amount of calcium per mole of calcium saccharide than is the case with calcium carbonate.

Some individuals have hypochlorhydria (low gastric secretion of acid), whereas others have achlorhydria (lack HCl in their gastric juice). Studies have shown that when these individuals swallow a calcium carbonate tablet, they simply excrete most of it instead of absorbing it. Such individuals are often diagnosed has having hypercalcemia because if the body lacks calcium, it will leave the bone tissue and circulate in the blood. Thus the blood has a measurable excess of calcium. It is believed that normal individuals, i.e. those who secrete acid in their gastrointestinal tract, easily absorb the calcium from calcium carbonate. Thus, researchers have postulated that individuals taking calcium carbonate orally apparently have to rely on their own gastrointestinal secretion of acid to convert this salt (which is insoluble in $H_2O$) into a soluble form of calcium, namely, calcium chloride for adsorption by the body. See, for instance, "The Absorption of Calcium Carbonate", Annals of Internal Medicine, Vol. 66, No. 5, Ivanovich, Fellows, and Rich, Pages 917–923 (May, 1967).

If water insoluble calcium carbonate cannot be converted to the soluble calcium chloride form supposedly due to lack of acid in the individual's gastrointestinal tract, then the oral administration must be of a soluble form of calcium. One suggestion has been to have calcium carbonate present in a tablet comprising an effervescent system. Effervescent systems are well known and an example is ALKA-SELTZER PLUS % disclosed in U.S. Pat. No. 4,083,950. Such systems contain an effervescent couple which typically comprises an alkaline material, such as sodium bicarbonate, sodium carbonate, potassium bicarbonate, potassium carbonate, and the like, together with an organic acid, such as citric acid, fumaric acid, adipic acid and the like. When the system is placed in water, the couple will react forming $CO_2$ and a water soluble salt. Since calcium carbonate is related to the carbonates of sodium and potassium, the use of $CaCO_3$ in an effervescent system seemed to be the obvious answer for providing a soluble form of calcium. Calcium carbonate was mixed with citric acid as an effervescent couple and the combination compressed into tablets. When these tablets were placed in water, they effervesced and there resulted an aqueous solution of soluble monocalcium citrate. See, for instance, Hunt and Johnson, "Relation Between Gastric Secretion of Acid and Urinary Excretion of Calcium After Oral Supplements of Calcium", Digestive Diseases and Sciences, Vol. 28, No. 5, Pages 417–421 (May, 1983). These authors deduced from the increased urinary output of calcium that when an individual drank this solution, the gastrointestinal tract readily absorbed the calcium which was now in the form of soluble monocalcium citrate.

However, problems have arisen with compressing these combination calcium carbonate/citric acid compositions into a stable, unitary tablet dosage form. Typically, calcium carbonate powder is blended with citric acid powder and a lubricant, and then the blend is charged directly to a tabletting press. However, difficulties arise when compacting these two components in admixture. In the presence of a little moisture, compacting the particles is facilitated as the water will act as a compression enhancing vehicle, but the water causes the two components to react as the two are stable (i.e. do not spontaneously react) only if kept substantially dry. It is well known to those skilled in the art that citric acid is incompatible with alkaline earth carbonates, such as calcium carbonate when water is present. (See Merck Index, 10th ed., (1983), page 2300). However, controlling moisture under manufacturing conditions is difficult. Moreover, as the moisture decreases, the "compression enhancing vehicle" effect of the water is lost and the particles tend not to stick during compacting. Of course, it is desired to have essentially no reaction until the tablet is placed into water just prior to ingestion.

Thus, to obviate instability in a unitary formulation, the two components may be physically separated from each other. In such compositions, some means is used to keep the active ingredients in the composition from contacting one another, such as film-coating the active ingredients with a suitable protective material or stratifying (layering) the active ingredients. However, when it is desired to have an effervescent composition, these techniques are often counterproductive.

Therefore a viable agent that would enhance tabletting and substantially inhibit degradation, yet not interfere with effervescence, would be desirable for calcium carbonate/citric acid formulations.

The prior art shows various agents used to enhance tabletting. Staniforth in U.S. Pat. No. 4,349,542 discloses a tabletting process using various tabletting agents such as lactose and Emdex (a spray-crystalized, maltose-dextrose direct tabletting sugar, supplied by K&K-Greeff Fine Chemicals Ltd., Croydon, U.K., manufactured by Edward Mendell, New York, U.S.A.), and McSweeney in U.S. Pat. No. 4,384,005, discloses a process to make an unsweetened beverage tablet using various tabletting agents such as tapioca dextrin (A. E. Staley #950SR, Decatur, Ill.) and maltodextrin (Mor Rex 1918).

However, the prior art does not disclose or suggest agents that not only enhance compression but also alleviate the degradation problems attendant effervescent systems comprising calcium carbonate/citric acid tablets.

OBJECT AND ADVANTAGES

The object of the invention is to provide a method that will allow calcium carbonate and citric acid to be directly compressed into a substantially stable, tablet dosage form, that will properly effervesce when placed in water. Also, a significant advantage of these tablets is that they provide a form of calcium that individuals with gastric problems can absorb. Also, some individuals have trouble swallowing tablets, and thus this invention provides a dosage form that effervesces in water so that such persons can drink the solution. This is particularly advantageous for older persons with osteoporosis who have trouble swallowing tablets.

SUMMARY OF THE INVENTION

The present invention provides for a directly compressible, substantially stable, calcium composition comprising approximately 7.5% to approximately 87.5% by weight calcium carbonate, approximately 10% to approximately 90% by weight organic acid component, and approximately 2.5% to approximately 18.5% by weight of a compression enhancing vehicle based on the combined weight of these three components, with the organic acid component being at least 80% by weight citric acid, and wherein the compression vehicle is coated on the calcium carbonate. Also, the present invention provides for a method of making a calcium composition comprising (a) coating calcium carbonate with a compression enhancing vehicle and (b) admixing the coated calcium carbonate with an organic acid component, said organic acid component being at least 80% by weight citric acid, thereby providing a substantially stable calcium carbonate/organic acid composition.

DETAILED DESCRIPTION OF THE INVENTION

Calcium carbonate, also known as carbonic acid calcium salt, occurs in nature as the minerals aragonite, calcite, and vaterite. In the present invention, it is preferred that the calcium carbonate used be in the calcite form and be essentially free of the aragonite crystal form. Small amounts of the aragonite form if present in $CaCO_3$/citric acid tablets will produce a loss of clarity or a slight haziness when effervescence has occurred after the tablets are placed in water.

The calcium carbonate employed in the present invention must be in the particulate form. An especially suitable particulate calcium carbonate is Albaglos®, supplied by Pfizer, at its facility in Adams, Mass. Albaglos is a precipitated calcium carbonate made by starting with high quality $CaCO_3$ and burning it to create $CO_2$ and CaO (lime). The CaO is dissolved in $H_2O$ to create a milk of lime solution $(CaCOH_{/2})$ The $CO_2$ (which was previously captured) is injected into the solution, causing pure crystals of $CaCO_3$ to precipitate.

The compression enhancing vehicle may be coated onto the particulate $CaCO_3$ by means such as (1) wet granulation (admixing the vehicle and $CaCO_3$ and then adding an appropriate amount of liquid to it, (2) dry granulation ("slugging" the vehicle and $CaCO_3$ together), (3) fluid bed granulation (spraying a liquid through the side of a canister onto a bed of the vehicle and $CaCO_3$, said canister having air coming in from the bottom to dry the slurry of fluid, vehicle, and $CaCO_3$ to a powder as it is floating in the air), and (4) spray drying (spraying an aqueous slurry of vehicle and $CaCO_3$ into a heated chamber which dries the slurry to a powder as it floats in the air). It is preferred that the compression enhancing vehicle is coated onto the calcium carbonate by spray drying.

The coated calcium carbonate particles must have an average particle diameter of less than approximately 400 microns, and more preferably less than approximately 250 microns. A particularly suitable average particle diameter is approximately 44 microns. The average thickness of the coating is not important and can vary from a few microns to several microns depending on the original size of the particulate $CaCO_3$. What is important is that the coated $CaCO_3$ particles be in the specified average particle diameter range. If the coated particle size is too large, then during effervescence the particles will settle down to the bottom of the water without reacting to form monocalcium citrate. Also, particles that are too large do not bind together well and compacting them into a tablet form becomes difficult. If the coated particles are too small, flowability and handling problems often occur.

After coating, the $CaCO_3$ is mixed with an organic acid component which must include citric acid and may include one or more other organic acids. It is preferred that the organic acid component be only citric acid or be a major amount (at least 80% by weight) of citric acid and a minor amount (less than 20% by weight) of the other organic acid. The preferred other organic acid is fumaric acid. Too much of an organic acid other than citric is not desirable because the taste of these other acids is not as pleasing as that of citric. The anhydrous form rather than the monohydrate form of citric acid is preferred.

The organic acid component should also be in the particulate form and should have a relatively larger average diameter than that of the $CaCO_3$. The selection of particle size is based on what is already known about effervescent systems employing these organic acids. The preferred distribution for average particle diameter is about $5\% \geq 840$ microns, about 250 microns$\leq 5\% \leq 840$ microns, about 74 microns$\leq 75\% \leq 250$ microns, and about 15%'3 74 microns.

The finished product tablet may contain anywhere from approximately 10–90% by weight coated calcium carbonate and approximately 90–10% by weight citric acid. However, these amounts should be stoichiometrically proportional so that the calcium carbonate and citric acid will essentially all react when the tablets are placed in water to form monocalcium citrate without there being any appreciable amount of leftover, unreacted calcium carbonate and/or citric acid. In a highly desired form, stoichiometrically balanced finished tablets are about 5 parts by weight coated $CaCO_3$ to about 6 parts by weight citric acid, based on the combined weight of citric acid and coated $CaCO_3$. Of course, if another alkaline material component is also used, such as sodium bicarbonate discussed below, additional citric or other organic acid will be needed to react with it.

The compression enhancing vehicle may be a maltodextrin either alone or in combination with a sugar. The disaccharide sugars, such as sucrose, lactose, maltose and the like are preferred. A very desirable vehicle is MALTRIN® M100 together with anhydrous lactose.

MALTRIN® M100 is a maltodextrin which is a hydrolyzed corn product (cereal solids) supplied by Grain Processing Corporation of Muscatine, Iowa. It is a bland, white, food grade carbohydrate with very desirable bulking and bodying characteristics. It has low sweetness, is readily soluble and is resistant to caking. A typical analysis of MALTRIN® M100 is as follows:.

| Typical Chemical and Physical Data | |
|---|---|
| Dextrose Equivalent | 9.0–12.0 |
| Moisture, % Max. | 6.0 |
| pH, 20% Solution | 4.0–4.7 |
| Form | White Powder |
| Typical Carbohydrate Profile (dry basis) | |
| Monosaccharides | 1% |
| Disaccharides | 4% |
| Trisaccharides | 6% |
| Tetrasaccharides | 5% |
| Pentasaccharides, & Above | 84% |

Other known excipients such as flavorings, vitamins (such as vitamin B or vitamin D), lubricants, surfactants, binders and the like may be optionally added into the tablet formulation of the present invention. Typical flavorings are grapefruit, lemon, and orange, and/or sweetners such as aspartame or sodium saccharin. A small amount of dioctylsodium sulfosuccinate (DOSS also known as docusate sodium) solution, for instance, may be added as a surfactant, and/or a small amount of fumaric acid may be added as a lubricant. These excipients are usually added in the amount of 0.001% to 5% weight/weight, more preferably 0.01% to 3% weight/weight, of the $CaCO_3$.

The composition may optionally contain one or more other typical effervescent couple components. For example, in addition to $CaCO_3$, the composition may include another alkaline material component such as sodium bicarbonate, sodium carbonate, potassium bicarbonate, potassium carbonate, or a mixture thereof, and in addition to the citric acid, the composition may include another organic acid such as fumaric acid, adipic acid, or a mixture thereof. As mentioned above, the presence of a minor amount of fumaric acid is desirable because it also acts as a lubricant.

When the tablets are placed in water, effervescence occurs releasing $CO_2$ and resulting in an aqueous solution of monocalcium citrate having a pH between about 4.0 and 4.5. The optimum pH is 4.3. Because the effervescent solution has a relatively acidic pH of about 4.0 to about 4.5, when it is ingested by an individual, the monocalcium citrate will resist precipitation while exposed to the higher pH values of the small intestine.

The formulation is substantially stable. By substantially stable, it is meant that the formulation will exhibit essentially no degradation to $CO_2$ and monocalcium citrate during long periods of storage, even when the storage temperature is above room temperature.

Examples of preferred embodiments of the present invention are set forth below. It is intended that they be only illustrative and the invention not limited thereby.

EXAMPLE I

A slurry was made of 41.5% weight/weight precipitated calcium carbonate (USP Albaglos®) having a average particle diameter of 0.8 microns, 5.0% weight/weight lactose, 3.5% maltodextrins (MALTRIN® M100, a hydrolyzed corn product supplied by Grain Processing Corporation) and 50.0% weight/weight water. The calcite crystal form of calcium carbonate was used. The slurry was spray-dried to a fine powder with a moisture level of less than 1.0% and a average particle diameter under 250 microns. About 5 parts by weight of this coated $CaCO_3$ was then admixed with about 6 parts by weight anhydrous citric acid powder in a quantity to provide approximately 75,000 tablets in the following manner. 115.208 kg of the coated $CaCO_3$ was mixed with 136.875 kg citric acid, 14.873 kg sorbitol, 15.000 kg lactose, 9.750 kg micronized fumaric acid, 0.533 kg calcium saccharin, 0.188 kg grapefruit flavor, and 0.075 kg glutamic acid in a ribbon blender for 10 minutes. The resultant admixture was then compressed into tablets of the desired dosage level, i.e. tablets having 1825 mg citric acid and 1250 mg of calcium carbonate (from about 1536 mg of coated $CaCO_3$) to provide about 500 mg of calcium. Compacting was done with a Colton-260 double rotary press.

When a tablet was placed in a glass of water, it effervesced. The calcium carbonate and the citric acid formed monocalcium citrate, having a pH between about 4 and 4.5.

EXAMPLE II

The procedure of Example I was followed, except that 5.0% weight/weight sucrose was used instead of lactose. These tablets compressed well, although not as well as the tablets made from the formulation of Example I.

EXAMPLE III

A slurry was made as follows. Precipitated calcium carbonate (USP Albaglos®) of the calcite crystalline form having 0.8 micron average particle diameter, anhydrous lactose and MALTRIN® M-100 were mixed and the mixture then added to water containing dioctylsodium sulfosuccinate (DOSS). The components were present in the amounts of 41.5% w/w precipitated calcium carbonate, 5.0% w/w anhydrous lactose, 3.5% w/w MALTRIN® M-100, 0.01% w/w DOSS, and 49.99% w/w water. The slurry was spray-dried to a fine powder of coated $CaCO_2$ having a moisture level less than 1% and a average particle diameter under 250 microns. The resultant coated $CaCO_3$ was then admixed with anhydrous citric acid powder in the amount of about 5 parts by weight coated $CaCO_3$ to about 6 parts by weight citric acid in the following manner. 200 g sodium bicarbonate (heat treated), 80.4 g fumaric acid (micronized), 7.1 g sodium saccharin, and 2.5 g grapefruit flavor were each weighed and passed through a 24 mesh screen to form a preblend. The preblend, 1506 g of the coated $CaCO_3$ powder, 2000 g citric acid (supplied by Miles Laboratories, Inc., Elkhart, Ind.), and 200 g lactose (USP Fast Flo Lactose, a spray dried mixture of alpha lactose monohydrate and amorphous lactose, supplied by Foremost-McKesson Foods Group, San Francisco, Calif.) were placed in a twin-shell mixer and mixed for 10 minutes. The resultant admixture was slugged (dry granulated) on a Kilian press having 1 inch diameter round, flat-faced beveled tooling. Then 3996 g of this granulation together with another 100 g sodium bicarbonate (heat treated) and 139 g fumaric acid (micronized) were passed with rough mixing through an oscillating granulator fitted with a 10 mesh screen. The resultant admixture was then placed in the twinshell mixer for 5 minutes. Next, the admixture was compressed into tablets of desired dosage level on the Kilian compactor having 1 inch round, flat-faced beveled tooling.

When a tablet was placed in water, the calcium carbonate reacted with the citric acid in an effervescent system creating monocalcium citrate solution. The pH of the solution was between 4 and 4.5.

These tablets and neat CaCO3 were tested in achlorhydric individuals and normal individuals, and the results are summarized in Tables IIIA and IIIB below.

In all of these Tables, x=mean absorption, S.D.=standard deviation, S.E.=standard error=S.D./√ # of people, p=probability, and the t-test regards the distribution in the two tails of the bell-shaped probability curve. No more than 5% of the data should be in the two tails of the bell, for a good statistical analysis. Well known statistical analysis methods were used for these calculations.

TABLE III A

FRACTIONAL CALCIUM ABSORPTION - ACHLORHYDRICS

| Patient | Effervescent Calcium | Calcium Carbonate |
|---|---|---|
| M.T. | .4092 | .0324 |
| G.S. | .4196 | .0375 |
| S.F. | .4125 | .0515 |
| R.R. | .5477 | .0666 |

These tablets and neat CaCO3 were tested in achlorhydric individuals and normal individuals, and the results are summarized in Tables IIIA and IIIB below.

In all of these Tables, x=means absorption, S.D.=standard deviation, S.E.=standard error=S.D./√ # of people, p=probability, and the t-test regards the distribution in the two tails of the bell-shaped probability curve. No more than 5% of the data should be in the two tails of the bell, for a good statistical analysis. Well known statistical analysis methods were used for these calculations.

TABLE III A

FRACTIONAL CALCIUM ABSORPTION - ACHLORHYDRICS

| Patient | Effervescent Calcium | Calcium Carbonate |
|---|---|---|
| M.T. | .4092 | .0324 |
| G.S. | .4196 | .0375 |
| S.F. | .4125 | .0515 |
| R.R. | .5477 | .0666 |
| E.Z. | .6579 | .0160 |
| H.Z. | .5714 | .0539 |
| D.C. | .5947 | .0833 |
| A.M. | .2581 | .0192 |
| M.P. | .3319 | .0255* |
| T.B. | .3244 | .0298* |
| J.L. | .4555 | .0440 |
| E.Z. | .6579 | .0160 |
| H.Z. | .5714 | .0539 |
| D.C. | .5947 | .0833 |
| A.M. | .2581 | .0192 |
| M.P. | .3319 | .0255* |
| T.B. | .3244 | .0298* |
| J.L. | .4555 | .0440 |
| $\bar{x}$* | .4530 | .0418 |
| S.D. | .1261 | .0207 |

TABLE III A-continued

FRACTIONAL CALCIUM ABSORPTION - ACHLORHYDRICS

| S.E. | .0380 | .0062 |
|---|---|---|

| t-test of Pairs | |
|---|---|
| $\Delta\bar{x}$ | −.4112 |
| $\Delta$S.D. | .1176 |
| $\Delta$S.E. | .0355 |
| t | 11.5988 (p < .0001) |

*Data from CaCO3 capsules used.

In Table III A is reported test data from achlorhydric patients. As can be seen, the mean absorption of effervescent calcium is 0.453 as compared to a mean absorption of 0.0418 calcium carbonate. This difference is more than ten-fold and is highly statistically significant with a t-value of 11.5988 and a probability of less than 0.0001.

The neat CaCO3 powder had originally been placed in gelatin capsules, and there was some concern about whether the gelatin capsules might somehow inhibit calcium absorption. Thus, repeat tests were conducted, and Table III A represents the repeat data except for the two starred subjects. The repeat tests were done by opening the capsules and pouring the neat CaCO3 powder out into distilled water, having the patients drink it and then rinsing. The two subjects that are starred are patients in whom the repeat CaCO3 absorption using the CaCO3 powder in distilled water were not done. Their CaCO3 absorption values were taken from the CaCO3 gelatin capsule data. The comparison in the other 9 subjects of CaCO3 gelatin capsules versus CaCO3 powder in distilled water showed no significant differences.

TABLE III B

FRACTIONAL CALCIUM ABSORPTION - NORMALS

| Patient | Effervescent Calcium | Calcium Carbonate |
|---|---|---|
| H.L. | — | .2762 |
| R.M. | .2481 | .2117 |
| M.L. | .3271 | .3661 |
| S.P. | .2658 | .0719 |
| R.B. | .4232* | .1230* |
| A.B. | .4154* | .0097* |
| E.K. | .2069 | .2400 |
| B.N. | .1979 | .0980 |
| A.W. | .2129 | .3125 |
| $\bar{x}$ | .2872 | .1899 |
| S.D. | .0914 | .1203 |
| S.E. | .0323 | .0401 |
| $\bar{x}$ | .2431** | .2252** |
| S.D. | .0487 | .1081 |
| S.E. | .0199 | .0409 |

| t-test of Pairs | |
|---|---|
| $\Delta\bar{x}$ | −.0264 |
| $\Delta$S.D. | .1070 |
| $\Delta$S.E. | .0437 |
| t | .6047 (not significant) |

*R.B. was found to be hypochlorhydric and A.B. was found to be achlorhydric on gastric analysis.
**Calculations were re-done excluding R.B. and A.B., as these two patients were obviously outliers having abnormal gastric acid.

Table III B shows the data obtained from the normals. Normal H.L. was not tested for effervescent calcium absorption. Also since in the "normals" that were studied, the average effervescent calcium absorption is 0.287, whereas the calcium carbonate absorption averages 0.1899, the data was recalculated excluding outliers R.B. and A.B., and Table III B shows that the mean calcium absorption recalculated from effervescent calcium is 0.2431 and from calcium carbonate is 0.2252. These absorption values are not statistically significantly different.

Excluding the 2 subjects R.B. and A.B. with abnormal stomach acid, a comparison of effervescent calcium absorption in normals (Table III B) with effervescent calcium absorption in achlorhydric patients (Table III A) reveals a significantly higher mean in the achlorhydric patients with a probability of less than 0.001.

Surprisingly, the data in Tables III A and III B shows that calcium absorption from effervescent calcium is not only better than from calcium carbonate in patients with achlorhydria, but it is better than absorption of either calcium carbonate or effervescent calcium in normal patients. One theory to explain the hyperabsorption in patients with achlorhydria is that these patients are known to have atrophic gastritis and perhaps the atrophic stomach wall is a poor filter for calcium when it exists in ionic form. Furthermore, the comparison of calcium carbonate and effervescent calcium in normals shows no significant difference. Therefore, it is a significant advantage of this invention to provide a form of calcium that individuals with gastric problems can absorb.

EXAMPLE IV

The procedure of Example III was repeated, except that anhydrous sucrose was used instead of anhydrous lactose. The resulting formulation compressed well into tablets, but not as well as the formulation made with lactose.

EXAMPLE V

Puffing

A decomposition product from the effervescent couple is $CO_2$ which will cause foil packaged tablets to puff. Tablets were made in the same manner as in Example III, except that (1) the amounts of fumaric acid employed were 90 g and 143.4 g instead of 80.4 g and 139 g, respectively, (2) 1 gram of the vitamin riboflavin was added with the grapefruit flavoring, and (3) 4006.6 g of the granulation instead of 3996 g was passed through the oscillating granulator. The tablets did not compress as well as those of Example III. Tablets of the formulation were packaged in twin-foil packets approximately 4.5 cm by 7 cm in size. The packets contain two tablets, side by side, and are airtight. Immediately after packaging, a packet has a thickness of approximately 0.55 to 0.65 cm. A stack having 10 packets (height 6.2 cm) piled one on top of another in a holder was stored at 50° C. (122° F.) in order to measure the extent of puffing caused as the amount of the $CO_2$ decomposition product increased. The height of the 10-packet stack was measured initially and then at intervals of 1 week and 4 weeks. The results are reported in the Table below:

TABLE V

| Puffing Height in Centimeters - Storage at 50° C. | | |
|---|---|---|
| | Storage Time | |
| Initial | 1 Wk. | 4 Wks. |
| 6.20 | 6.50 | 8.00 |

It can be seen from the above data that tablets according to the invention have substantially good storage stability.

As discussed in the Background section above (see the reference to the Merck Index) an alkaline earth carbonate (i.e. calcium carbonate) and citric acid by themselves simply would not be storage stable in each other's presence, but would react at room temperature to form $CO_2$, due to some moisture being trapped as the foil packets are sealed.

We claim:

1. A directly compressed substantially stable effervescent tablet calcium composition comprising approximately 7.5% to approximately 87.5% by weight calcium carbonate having an average particle diameter under approximately 400 microns, approximately 10% to approximately 90% by weight uncoated organic acid component having a relatively larger average diameter than that of the calcium carbonate, and approximately 2.5% to approximatley 18.5% by weight of a compression enhancing vehicle which is maltodextrin, a disaccharide sugar, or a mixture thereof, based on the combined weight of these three components, with the organic acid component being at least 80% by weight citric acid, and wherein the compression vehicle is coated on the calcium carbonate.

2. The composition of claim 1, wherein the the organic acid component is citric acid, or is citric acid and a minor amount of fumaric acid, adipic acid, or a mixture thereof.

3. The composition of claim 2, wherein the compression vehicle consists essentially of 2–8% maltodextrin and 4–13% disaccharide sugar based on the combined weight of maltodextrin, disaccharide sugar, citric acid, and calcium carbonate.

4. The composition of claim 3, wherein the disaccharide sugar is selected from the group consisting of sucrose, lactose, maltose, and a mixture thereof.

5. The composition of claim 4, wherein the organic acid component consists essentially of a major amount of citric acid and a minor amount of fumaric acid.

6. The composition of claim 5, further including a minor amount of an excipient selected from the group consisting of a surfactants, vitamins, flavorings, binders, lubricants buffering agents, or a mixture thereof.

7. The composition of claim 6, wherein the surfactant is dioctylsodium sulfosuccinate present in an amount of from 0.001% to 5% on a weight/weight basis with the calcium carbonate.

8. The composition of claim 7, further including a minor amount of an alkaline material component selected from the group consisting of sodium bicarbonate, sodium carbonate, potassium bicarbonate, potassium carbonate, or a mixture thereof.

9. The composition of claim 8, wherein the flavoring is grapefruit, orange, lemon, aspartame, sodium saccharin or a mixture thereof.

10. The composition of claim 1 wherein the calcium carbonate has an average particle diameter under approximately 250 microns

* * * * *